(12) United States Patent
Abercrombie et al.

(10) Patent No.: US 10,646,265 B2
(45) Date of Patent: May 12, 2020

(54) HEAT EXCHANGER UNIT FOR CRYOTHERAPY

(71) Applicant: Cryotherapeutics GmbH, Cologne (DE)

(72) Inventors: Stuart Robert Abercrombie, Milton (GB); Duncan Aleck Bishop, Huntingdon (GB); Symon Cotton, Over (GB); Richard Day, Great Cambourne (GB); Sylvain Bruno Jamais, Ely (GB); Simon Karger, Ely (GB); Andrew Lintott, Ely (GB); Nathan Wrench, Cambridge (GB)

(73) Assignee: Cryotherapeutics GmbH, Cologne (DE)

( * ) Notice: Subject to any disclaimer, the term of this patent is extended or adjusted under 35 U.S.C. 154(b) by 784 days.

(21) Appl. No.: 15/120,841

(22) PCT Filed: Dec. 15, 2014

(86) PCT No.: PCT/EP2014/077773
§ 371 (c)(1),
(2) Date: Aug. 23, 2016

(87) PCT Pub. No.: WO2015/124232
PCT Pub. Date: Aug. 27, 2015

(65) Prior Publication Data
US 2016/0361106 A1 Dec. 15, 2016

Related U.S. Application Data

(60) Provisional application No. 61/943,611, filed on Feb. 24, 2014.

(51) Int. Cl.
*A61B 18/02* (2006.01)
*A61M 5/44* (2006.01)
(Continued)

(52) U.S. Cl.
CPC .......... *A61B 18/02* (2013.01); *A61M 5/1486* (2013.01); *A61M 5/44* (2013.01);
(Continued)

(58) Field of Classification Search
CPC ............ A61B 18/02; A61B 2018/0022; A61B 2018/00422; A61B 2018/0212;
(Continued)

(56) References Cited

U.S. PATENT DOCUMENTS 2,842,123 A * 7/1958 Rundhaug ............ A61M 5/1486
604/141
6,547,811 B1 * 4/2003 Becker ...................... A61F 7/02
604/113
(Continued)

FOREIGN PATENT DOCUMENTS

| EP | 1259204 | 11/2002 |
|---|---|---|
| WO | WO 2002038065 | 5/2002 |
| WO | WO 2012140439 | 10/2012 |

OTHER PUBLICATIONS

Written Opinion in International Application No. PCT/EP2014/077773, dated Mar. 30, 2015, 7 pages.

*Primary Examiner* — Thomas A Giuliani
*Assistant Examiner* — Christine A Dedoulis
(74) *Attorney, Agent, or Firm* — Sunstein LLP

(57) ABSTRACT

Disclosed herein is an apparatus for cooling a sterile liquid for use in cryotherapy, the apparatus comprising: a first chamber (202) adapted to receive a removable container (201) of sterile liquid and a fluid port for receiving a fluid for applying, in use, pressure to a received removable container (201); and a second chamber (203) comprising a cooler; wherein the first chamber (202) is arranged to be in thermal conductivity with the second chamber (203) such that, in use, the contents of the first chamber (202) are cooled by the cooler of the second chamber (203). Advantageously, (Continued)

embodiments provide a system, heat exchanger unit within the system and method for supplying a sterilised working fluid to a catheter system for cryotherapy, the working fluid being supplied at a desired and easily controllable temperature and flow rate.

12 Claims, 3 Drawing Sheets

(51) Int. Cl.
*A61M 5/148* (2006.01)
*A61B 18/00* (2006.01)

(52) U.S. Cl.
CPC .......... *A61B 2018/0022* (2013.01); *A61B 2018/00422* (2013.01); *A61B 2018/0212* (2013.01)

(58) Field of Classification Search
CPC ........... A61B 18/0206; A61B 18/0218; A61B 2018/0225; A61B 2018/0231; A61B 2018/0237; A61B 2018/0243; A61B 2018/025; A61B 2018/0256; A61B 2018/0262; A61B 2018/0268; A61B 2018/0275; A61B 2018/0281; A61B 2018/0287; A61B 2018/0293; A61M 5/1486; A61M 5/44; A61M 2025/0001; A61M 2025/0004
USPC .................................................. 606/20–26
See application file for complete search history.

(56) References Cited

U.S. PATENT DOCUMENTS

| | | |
|---|---|---|
| 6,602,246 B1 | 8/2003 | Joye |
| 6,673,066 B2 | 1/2004 | Werneth |
| 6,955,174 B2 | 10/2005 | Joye et al. |
| 2002/0099365 A1 | 7/2002 | Joye |
| 2003/0125665 A1* | 7/2003 | Rosenman ....... A61B 17/00491 604/113 |
| 2005/0203598 A1 | 9/2005 | Becker et al. |
| 2008/0119791 A1* | 5/2008 | Cazzini .................. A61M 5/14 604/151 |
| 2011/0190751 A1* | 8/2011 | Ingle ..................... A61B 18/02 606/21 |
| 2012/0197245 A1* | 8/2012 | Burnett ................. A61B 18/02 606/21 |
| 2012/0283562 A1* | 11/2012 | Ginsburg ................. A61F 7/12 600/435 |
| 2013/0310823 A1* | 11/2013 | Gelfand ............. A61B 18/1492 606/33 |

* cited by examiner

HEAT EXCHANGER UNIT FOR CRYOTHERAPY

CROSS-REFERENCE TO RELATED APPLICATIONS

This Application is a U.S. national stage entry under 35 USC § 371 of PCT/EP2014/077773, filed Dec. 15, 2014, which itself claims priority to U.S. Provisional Patent Application 61/943,611, filed Feb. 24, 2014, both of which are incorporated herein by reference in their entireties.

BACKGROUND OF THE INVENTION

From the late 1970s, cryotherapy has been used in the cardiovascular system starting from, for example, 1977 when it was used to surgically treat cardiac arrhythmias. Over the ensuing years it became widely recognised that cryotherapy was particularly advantageous for working in the heart. Its safety and efficacy was unsurpassed as surgeons were able to ablate delicate cardiac structures such as the A-V node, pulmonary veins and delicate peri-nodal atrial tissue without concern for thrombosis, perforation or other adverse events.

More recently, researchers have started investigating the use of cryotherapy in the vascular system as a method to treat calcified plaque. Clinical data published by Laird et. al. "Cryoplasty for the Treatment of Femoropopliteal Arterial Disease: Extended Follow-up Results" J ENDOVASC THE 2006; 13 (Suppl II): 11-52-11-59 has shown that cryotherapy achieves good clinical results when used in highly stenosed vessels of the peripheral vasculature.

Much of this previous work has been in treating calcified plaque in patients with calcified highly stenosed vessels (>70% stenosis) as an alternative to drugs, balloon angioplasty, stents or other conventionally used therapies.

Cryotherapy typically involves applying cooling to a vessel using a catheter based balloon. A refrigerant is used to expand a balloon into contact with a target. The temperatures used in treating such calcified highly stenosed blood vessels usually range from −10° C. to −20° C. (263K to 253K) and are generally warmer than those used in the ablation field (such as those used to treat arrhythmia or for cancer tumor ablation) where refrigerant temperatures will generally be colder than −70° C. (203K). Typically, the pressure in the balloon will be above 5 atmospheres (ATM), 507 kPa, as the goal of therapies such as angioplasty is to force open critically stenosed calcified vessels.

There has also been some interest in using cryotherapy on non-critically stenosed plaque typical of so called vulnerable or unstable plaque, as exemplified by U.S. Pat. Nos. 6,673,066, 6,602,246 and 6,955,174. Vulnerable plaque, or unstable plaque, may be defined as a non-flow limiting plaque which is lipid rich with a thin cap fibroatheroma. For the purposes of the present document the terms vulnerable and unstable plaque are used interchangeably.

When such vulnerable plaque ruptures, a thrombus forms and causes a heart attack. A discussion, description and characteristics of these types of plaques is reviewed in Libby, "Atherosclerosis: The New View" Scientific American, May 2002, pg. 47. In some early work, the biological effect was poorly understood and improperly described as, for example, in U.S. Pat. No. 6,955,174 where cryotherapy treatment is described which "inhibits release of the retained fluid into the blood vessel". It is now thought that this mechanism is incorrect and that a ruptured plaque does not release materials into the bloodstream but causes a thrombus to form at the site of rupture. This mechanism is described by Muller, "Presentation at Cardiovascular Revascularization Therapies", March 28-31, 2005, Washington D.C., and by Fuster et al, "Atherothrombosis and High Risk Plaque", Journal of the American College of Cardiology, 2005, Vol. 46, No. 6, pp. 937-54.

WO2012/140439 A1 discloses a known system for performing cryotherapy. A balloon catheter is positioned at a site of vulnerable plaque in a patient. A working fluid is supplied to the balloon catheter via a conduit. The working fluid may be used both as a coolant of the balloon and also to inflate the balloon. The working fluid is pumped from a reservoir and through a heat exchanger that cools the working fluid to a temperature for cryotherapy, that may be −30° C. or lower in order to achieve a sufficiently low temperature where the balloon contacts the vessel wall.

In order to perform cryotherapy, the flow rate and temperature of the working fluid supplied to the balloon need to be accurately controlled. The pressure of the fluid used to inflate the balloon of the catheter, which may be the same working fluid, also needs to be accurately controlled.

It is necessary for the working fluid to be sterile in order to limit any harm caused by an accidental leak of the working fluid from the catheter system into a patient's body. Even a small leak of a non-sterile fluid is clinically unacceptable. In order to ensure that the working fluid is sterile, it has been tried to provide inline aseptic medical filtering of the working fluid at the entry point of the catheter to a patient's body. However, when the aseptic filtering was provided in the fluid path, trials revealed the need for unexpectedly high working fluid supply pressures, resulting in the problem of the required flow rate and temperature of the working fluid being difficult to achieve.

Without the inline medical filter, the working fluid would only be sterile if all working fluid contacting parts in the pump and heat exchanger were sterilised prior to each use of the system. Clearly such sterilisation operations would be very time consuming, expensive and inconvenient. Moreover, it is not economically or practically feasible for the pump and heat exchanger to be disposable devices that are only used once since, due to the required conditions for cryotherapy, the devices need to be of a very high quality.

There is therefore a need for an improved technique for supplying a working fluid that is sterile as well as at a desired temperature and flow rate for cryotherapy.

SUMMARY OF THE INVENTION

According to a first aspect of the invention, there is provided an apparatus for cooling a sterile liquid for use in cryotherapy, the apparatus comprising: a first chamber adapted to receive a removable container of sterile liquid and a fluid port for receiving a fluid for applying, in use, pressure to received removable container; and a second chamber comprising a cooler; wherein the first chamber is arranged to be in thermal conductivity with the second chamber such that, in use, the contents of the first chamber are cooled by the cooler of the second chamber.

Preferably, the cooler is provided by a fluid coolant within the second chamber; and the first and second chambers are configured such that there is no fluid communication between the first and second chambers. Advantageously, flooding of the second chamber with the liquid coolant ensures good thermal transfer to the first chamber.

Preferably, the fluid coolant is at a temperature of 0° C. or lower. Advantageously, the liquid coolant maintains the required low temperature within the second chamber throughout the procedure.

Preferably, the apparatus further comprises a conduit for providing a supply of fluid to the fluid port of the first chamber.

Preferably, the conduit passes through the second chamber; and the conduit is arranged in coils in the second chamber. Advantageously, this ensures that the temperature of the fluid is in equilibrium with that of the second chamber as it enters the first chamber.

Preferably, the fluid coolant is ethane.

According to a second aspect of the invention, there is provided a container for supplying a sterile fluid to a catheter for use in cryotherapy, the container comprising a reservoir comprising a sterile fluid that is a liquid at a temperature below 0° C.; wherein, in use, the reservoir is configured to reduce in volume in response to an applied pressure to the container such that the sterile fluid flows out of the container; and the container is configured to be inserted into, and removed from, a receiving chamber for cooling the sterile fluid within the reservoir.

Preferably, the reservoir of the container is a compressible bag.

According to a third aspect of the invention, there is provided a component of a catheter system for use in cryotherapy, the component comprising: a container as described above; and an umbilical conduit for carrying a flow of fluid from the container.

According to a fourth aspect of the invention, there is provided a cryogenic cooling system, comprising the above described apparatus; and a pressuriser arranged to pressurise a fluid in the first chamber.

Preferably, the pressuriser is configured to pressurise a fluid within the first chamber to pressures up to 20000 kPa or more.

Preferably, the pressuriser is a positive displacement pump.

Preferably, the system further comprises a supply of coolant arranged to supply a coolant to the second chamber at a temperature of 0° C. or lower.

Preferably, the system, further comprises the above-described container inserted into the first chamber of the apparatus.

According to a fifth aspect of the invention, there is provided a method of providing a supply of sterile coolant for use in cryotherapy, the method comprising: supplying a coolant to the second chamber of an apparatus according to any of the above-described methods, wherein the coolant is at a temperature of 0° C. or lower; inserting the above-described container into the first chamber of the apparatus; supplying a fluid to the first chamber; waiting for the fluid within the container to cool to a predetermined temperature; and pressurising the fluid in the first chamber to thereby cause fluid within the container to flow from the container.

Preferably, the method comprises supplying the first fluid to the first chamber without applying a significant pressure to the container.

Preferably, the predetermined temperature is 0° C. or less.

Preferably, the method further comprises pressurising the fluid in the first chamber to a pressure of 20000 kPa or more.

According to a sixth aspect of the invention, there is provided a method of controlling the above-described system, the method comprising automatically controlling the flow rate of fluid out of the container by automatically controlling the pressure of the fluid in the first chamber.

According to a seventh aspect of the invention, there is provided an apparatus and/or system for providing a supply of sterile fluid for use in cryotherapy substantially as shown in any of the appended FIGS. 1 to 4.

DETAILED DESCRIPTION OF THE DRAWINGS

Embodiments of the present invention will now be described in detail with reference to the accompanying drawings, in which.

Figure 3:
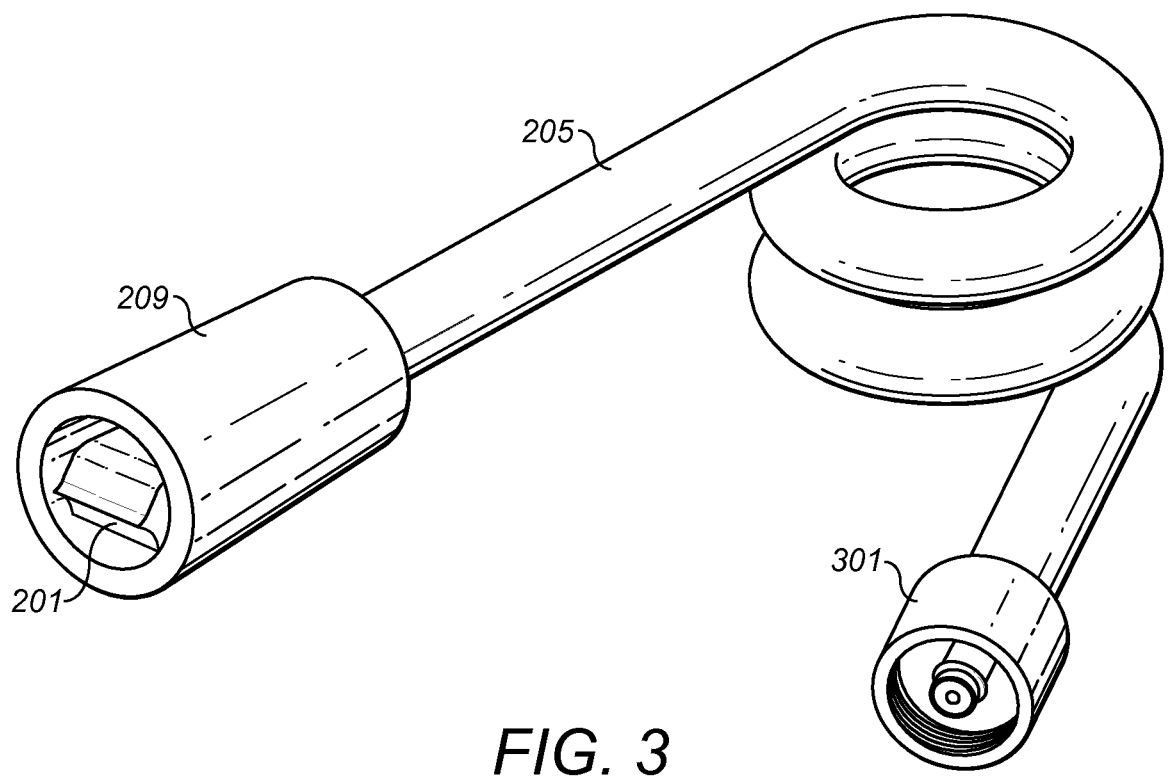
Figure 4:
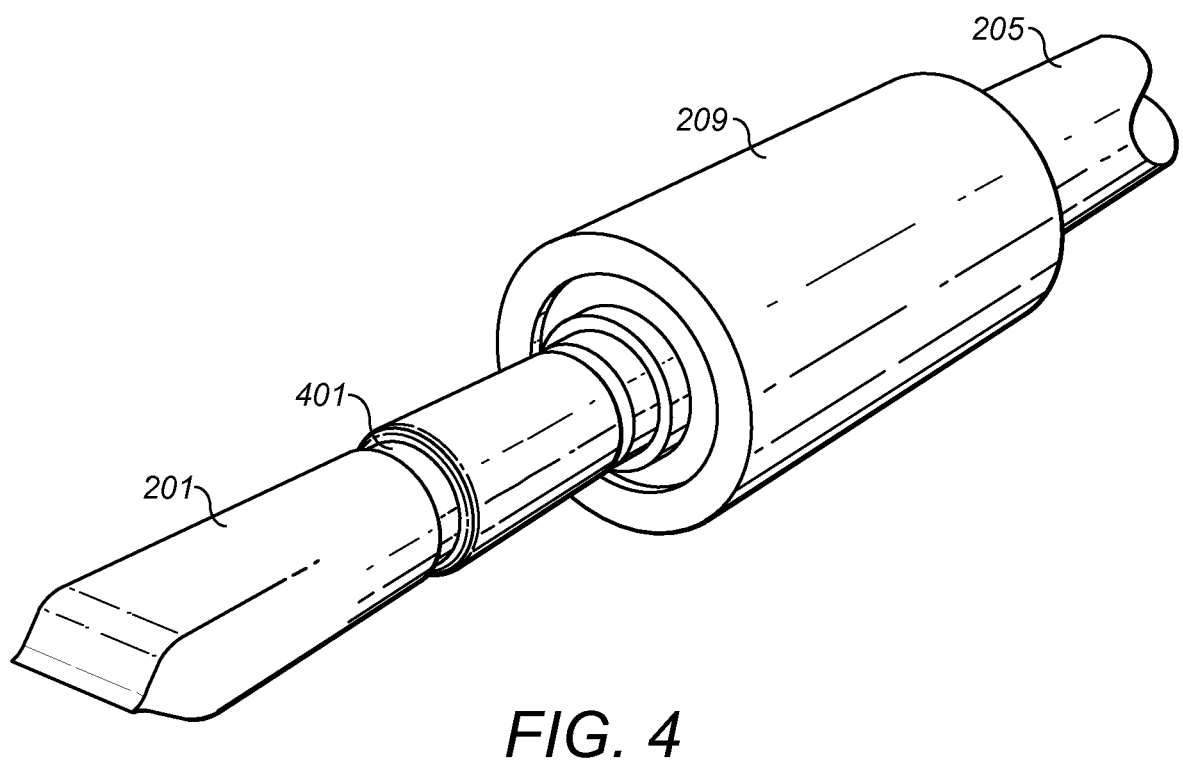

FIG. 3 shows a working fluid container 201 with the umbilical 205 part of a catheter system according to an embodiment; and FIG. 4 shows a working fluid container 201 according to an embodiment.

DETAILED DESCRIPTION

Embodiments of the invention provide a system, heat exchanger unit within the system and method for supplying a sterilised working fluid to a catheter system for cryotherapy, the working fluid being at a desired and easily controllable temperature and flow rate.

Figure 1:
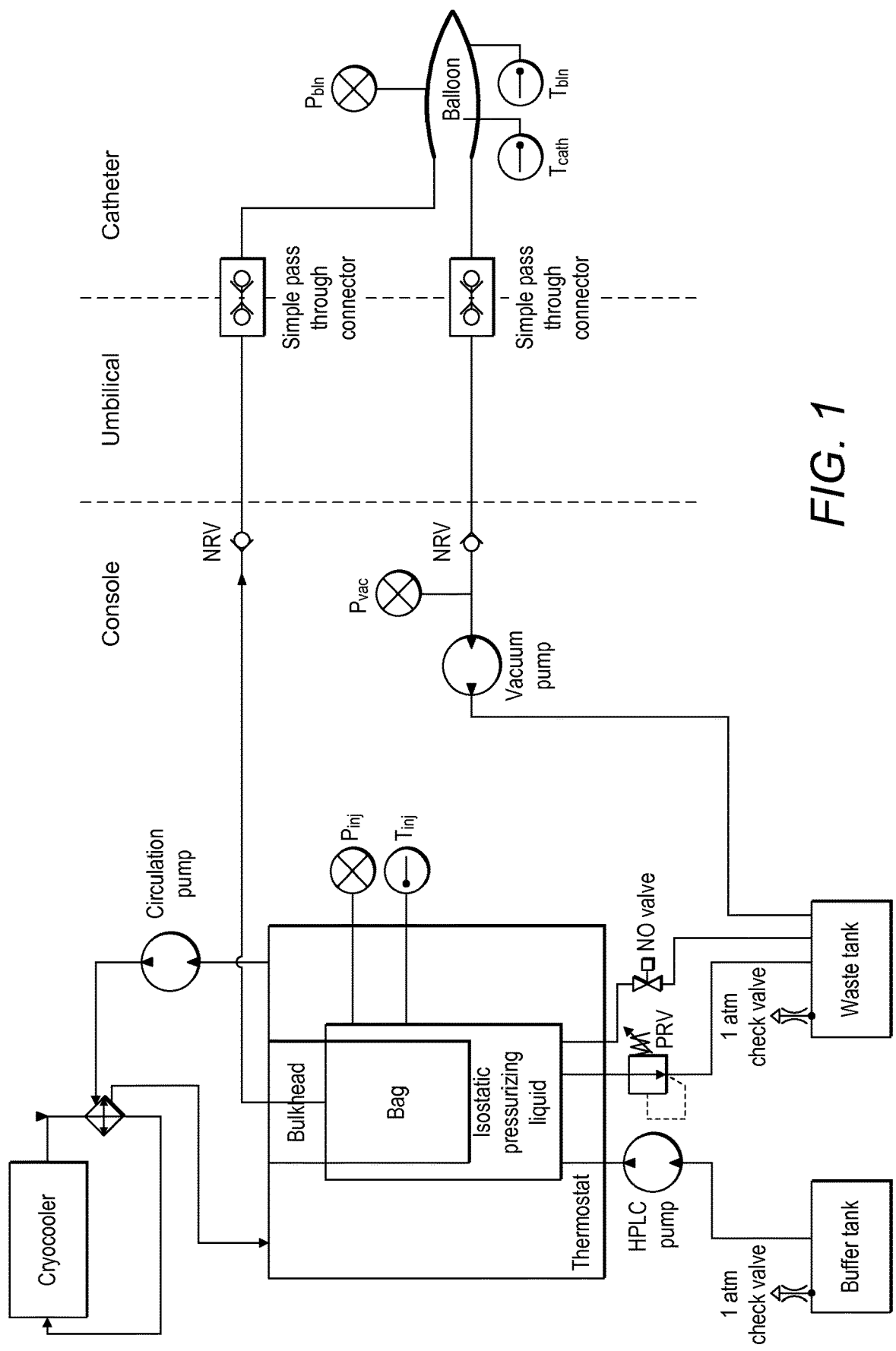
FIG. 1 shows a system for providing a working fluid to a catheter according to an embodiment.

FIG. 1 shows a system according to an embodiment. The console part of the system provides a supply of sterile working fluid to a catheter at the desired temperature and pressure for performing cryotherapy. Advantageously, there is no inline filter in the system and so the pressure required to achieve a desired flow rate is not so high that it causes problems. In addition, the temperature and flow rate of the working fluid at the catheter proximal end closely correspond to the temperature and flow rate of the working fluid output from the console. The temperature and flow rate of the working fluid can therefore be accurately controlled without the pressure of the working fluid being unacceptably high.

The console comprises a heat exchanger unit, that is operated as a chiller unit, to generate a supply of sterile working fluid at an easily controllable temperature and flow rate.

FIG. 1 shows an exemplary implementation of a system comprising the heat exchanger unit. Numerous modifications and variations to the shown system are possible that still provide the required operation of a cryotherapy system according to an embodiment. For example, although an HPLS pump is shown, any pressurizing pump may be used. Similary, although a Cryocooler is shown, any cryosource may be used. Also, FIG. 1 does not show details of the design of the catheter or a vessel that the balloon of the catheter is acting on. The skilled person would be aware of a number of balloon cather designs that that are suitable for such applications.

Figure 2:
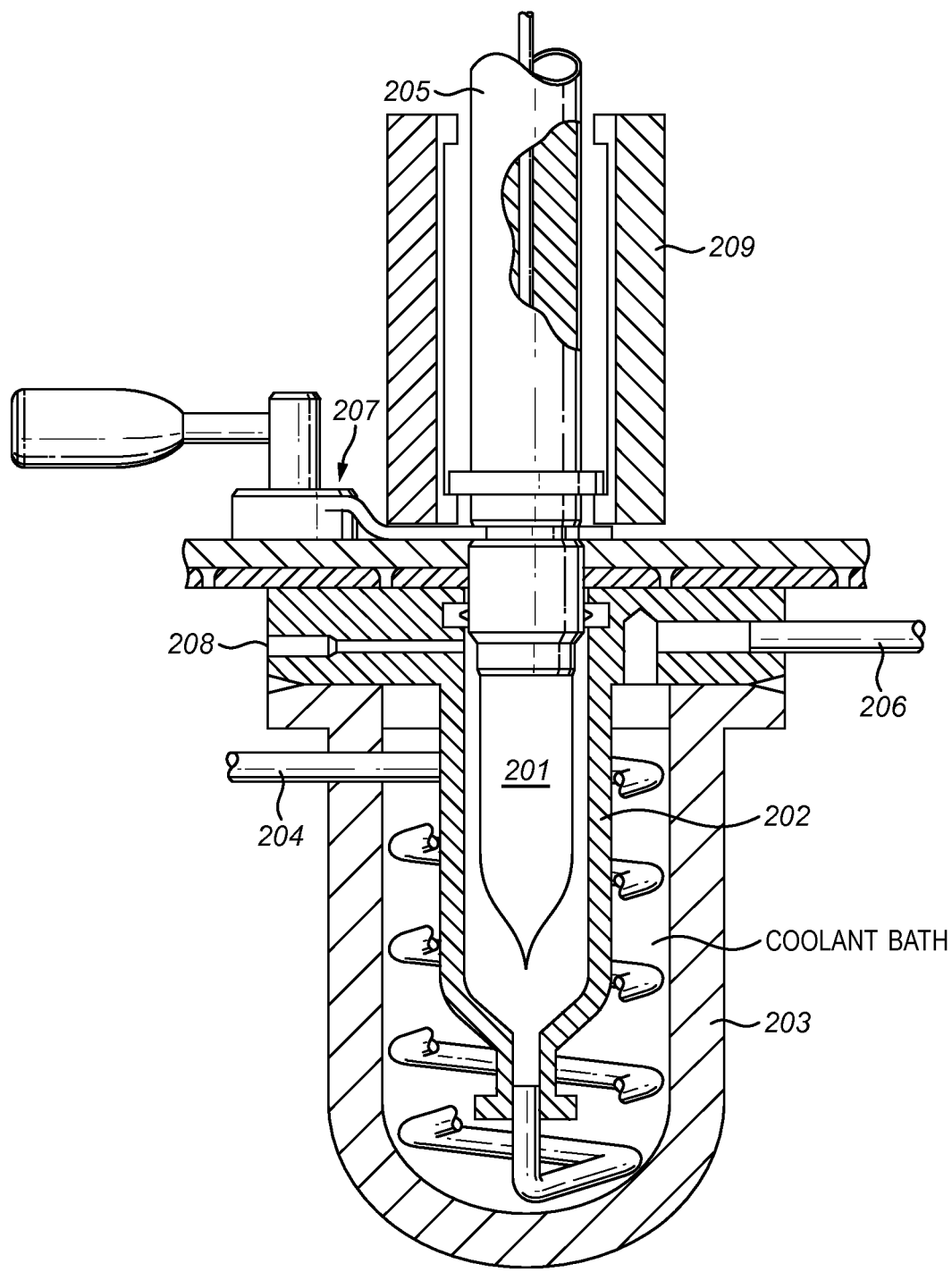
FIG. 2 shows a heat exchanger unit for providing a working fluid to a catheter according to an embodiment.

A heat exchanger unit according to an embodiment of the invention is shown in FIG. 2.

The heat exchanger unit comprises an inner chamber 202 with a substantially U-shaped cross-section. The heat exchanger unit also comprises an outer chamber 203 with a substantially U-shaped cross-section. The inner chamber 202 is arranged mostly within the outer chamber 203. The inner chamber 202 is preferably made of a metal so that there is high thermal conductivity between the inside of the outer chamber 203 and the inside of the inner chamber 202. Preferably the outer chamber 203 is made of, or lined on its outside with, a thermally insulating material. A conduit 204 is provided for supplying a fluid to the inner chamber 202. A separate conduit 206 is provided for supplying a fluid to the outer chamber 203. The walls of the inner chamber 202 are impermeable to the fluids of the inner and outer chambers and there is no fluid communication between the inner and outer chambers.

Although this is not shown in FIG. 2, the heat exchanger unit also comprises a source of fluid supplied to the inner chamber 202 and a pressuriser of the fluid in the inner chamber 202. Preferably, the source and pressuriser are able to supply the fluid at a flow rate of up to 200 ml/minute or more and to pressurise the fluid at pressures up to 20000 kPa or more. Preferably, the pressuriser is a positive displacement pump. The pump may be of syringe or piston type or have a gear configuration. Preferably, the source and pressuriser the fluid are thermally insulated and/or sufficiently physically separated from the outer chamber 203 so that they are not exposed to the low temperatures within the outer chamber 203.

The fluid that is supplied to the inner chamber 202 is preferably a liquid over the entire operational temperature range for cryotherapy. The fluid therefore remains a liquid over temperatures of at least 0° C. to −30° C. and preferably to temperatures up to 50° C. and as low as −70° C., more preferably to temperatures as low as −120° C. The effect of the fluid remaining a liquid during operation is that there is pressure equilibrium at all times on either side of the bag containing the sterile fluid, thereby removing a lot of the structural integrity requirement that a pressurized rigid container would have to meet. A bag design of the sterile fluid consumable can therefore be used. A suitable fluid may comprise a perfluorocarbon.

Although not shown in FIG. 2, the heat exchanger unit also has a source of a coolant arranged to supply a coolant to the outer chamber 203 through the conduit 206. The coolant supplied to the outer chamber 203 may be ethane or any of a number of different coolants that are known in the art. However, the coolant may be any fluid that remains in its liquid phase throughout the range of temperatures required in the first and second chamber to achieve the temperatures required at the balloon for the desired therapeutic effects.

Coolants that change to their gas phase upon warming up are also adequate as long as they are in a liquid state when in the range of temperatures required in the first and second chamber for the desired therapeutic effects. The outer chamber 203 preferably provides a bath of a coolant liquid that the inner chamber 202 sits in. The coolant may be cooled using, for example, a single or multistage compressor or a Stirling engine or any other appropriate means of cooling.

At the top of the inner chamber 202 is an input port. As shown in FIG. 2, a container 201 of working fluid has been inserted into the inner chamber 202 through the input port. The shown container 201 has a flexible bag and is connected to an umbilical conduit 205 of a catheter system. The bag of the container 201 is a reservoir of sterile working fluid. The walls of the bag are impermeable and there is no fluid communication between the working fluid within the container 201 and the pressurizing fluid in the inner chamber 202. The sterile contents of the bag are therefore not contaminated by the pressurizing fluid in the inner chamber 202. The bag provides a predetermined volume of working fluid. The volume is sufficient for a single cryotherapy procedure. The bag is made from a material that is stable and retains its flexibility at cryogenic temperatures. A suitable material for manufacturing the bag from is a high-performance Teflon® FEP film, that is a melt-processable copolymer of tetrafluoroethylene and hexafluoropropylene. Preferably, the sterile working fluid remains in a liquid state over the entire operational temperature range, including body temperature and initial cryogenic temperature. The working fluid may comprise a perfluorocarbon or alcohol.

In use, a coolant is supplied to the outer chamber 203 and the outer chamber 203 is cooled. The temperature of the outer chamber 203 will typically be a lot lower than 0° C. The coolant cools the walls of the inner chamber 202. A container 201 of working fluid is inserted into the heat exchanger unit through the input port of the inner chamber 202, prior to any fluid being supplied to the inner chamber 202. A fluid is then supplied to the inner chamber 202 so as to fill the air gap between the bag of the container 201 and the walls of the inner chamber 202. The fluid supplied to the inner chamber 202 is cooled by the walls of the inner chamber 202 and the fluid in turn cools the bag and thereby the sterile working fluid in the bag of the container 201 is cooled. When the sterile working fluid has cooled to a desired temperature for use in cryotherapy, on demand from the surgeon, more fluid is supplied to the inner chamber 202 to pressurise the bag of the container 201. The effect of pressurising the bag causes the sterile working fluid to flow from the bag into the umbilical 205 of the catheter system. The flow rate of the working fluid increases with the pressure of the fluid in the inner chamber 202. The pressure may be as high as 20000 kPa in order to provide an adequate flow rate to provide sufficient cryoenergy at the balloon. After the operation of supplying the sterile fluid has been completed, the fluid in the inner chamber 202 is evacuated. This may be performed, for example, by reversing the operation of a pump that has supplied the fluid. The evacuated fluid may flow into a waste tank for disposal or may be stored for reuse. The used container 201 of working fluid is then removed from the heat exchanger unit. Evacuating the fluid in the inner chamber prior to removing the container 201 from the heat exchanger unit advantageously avoids, or limits, the exposure of a user to a fluid at a cryo temperature.

Advantageously, a flow of sterile working fluid is provided. The flow rate of the working fluid increases with the pressure of the fluid supplied to the inner chamber 202 and therefore easily controlled by controlling a pump, or any other type of pressuriser, for the supply of pressurising fluid to the inner chamber 202.

The temperature of the working fluid is also easily controlled by the temperature of the coolant in the outer chamber 203 and the time that the bag is immersed in the fluid in the inner chamber 202.

The container 201 of sterile working fluid may be used for a single operation and then disposed of. To generate a further supply of sterile working fluid, an unused container 201 of sterile working fluid can be inserted into the heat exchanger unit and the above-described operations easily repeated. The container 201 may be pre-cooled before being inserted into the heat exchanger unit so that it is not necessary for a user to wait for the contents of the container 201 to cool. Alternatively, or in addition, there may be more than one heat exchanger per system and a reconnection to an unused container 201 rapidly made, without the need to replace and reinsert the catheter into a body.

The outer chamber 203 may be maintained at the required low temperature over an extended period of time during which a plurality of applications of the sterile working fluid are performed. The volume of working fluid that can be supplied to the catheter system is inherently limited by the volume of working fluid within the container 201. Having a limit on the amount of working fluid that can be supplied to a catheter system is an important safety feature as it limits the amount of working fluid that can flow into a patient if a leak occurs in the catheter system.

Preferably, the conduit 204 that supplies the fluid to the inner chamber 202 has a coiled arrangement within the outer chamber 203, as shown in FIG. 2. The part of the conduit 204 within the outer chamber 203 is preferably made of metal and has a high thermal conductivity. The fluid within conduit 204 is cooled by the coolant as the conduit 204 passes through the outer chamber 203. Advantageously, the coiled arrangement of the conduit 204 increases the length of the conduit 204 within the coolant and the amount of cooling that the fluid within the conduit 204 experiences is therefore increased, bringing the pressurizing fluid in temperature equilibrium with the outer chamber before entering the inner chamber. This enables the removal of any detrimental warming effect of the sterile fluid from the injection of the pressurising fluid into the inner chamber.

Preferably, the volume of the fluid within the coils of the conduit 204 is greater than or equal to the volume of working fluid within the bag.

Preferably, the inner chamber 202 also has a flow path 208 from the chamber to a valve, such as a bleed valve, for allowing air within the inner chamber 202 to exit when fluid is supplied to the inner chamber 202.

Preferably, one or more pressure sensors are provided that are configured to measure the pressure within the inner chamber 202. The one or more pressure sensors may be provided, for example, at the end of the flow path 208 or anywhere within the inner chamber 202. The one or more pressure sensors are preferably connected to the pressuriser of the fluid in the inner chamber 202. The feedback of a measured pressure from within the inner chamber 202 allows the pressure of the fluid to be easily, and automatically, controlled.

The one or more pressure sensors may include open hydraulic tubes, piezoelectric transducers, fibre-optic transducers or other type of sensors.

Preferably, one or more temperature sensors are provided that are configured to measure the temperature within the inner chamber 202. The one or more temperature sensors may be provided anywhere within the inner chamber 202. The feedback of a measured temperature from within the inner chamber 202 aids the control of the cooling by the outer chamber 203 and the determination of the temperature of the sterile working fluid within the bag.

Although not shown in FIG. 2, the outer surface of the outer chamber 203 would preferably be covered in thermal insulation or the walls of the chamber itself be made from a material that is sufficiently insulating.

Although not shown in FIG. 2, the heat exchanger unit has a housing for its components.

FIG. 3 shows the container 201 of working fluid according to an embodiment. The shown container 201 is integral with an umbilical 205 of a catheter system. The container 201 is located at one end of the umbilical 205 and it surrounded by a retractable insulated safety sheath 209. The other end of the umbilical 205 has a screw connector 301 for connecting the umbilical 205 to another part of a catheter system.

FIG. 4 shows the container 201 in FIG. 3 with the sheath 209 retracted. The sheath 209 is retracted in such a manner when the bag of the container 201 is inserted into the heat exchanger unit, as shown in FIG. 2. Preferably, a seal 401 is provided at the neck of the bag.

In an alternative embodiment, the container 201 is not integral with an umbilical 205 but has a connector for connecting the container 201 to the umbilical 205. The same connector may also connect the container 201 to the heat exchanger unit or a further connection mechanism may be provided for this purpose. In the embodiment shown in FIG. 2, a CAM lock 207 is used to connect the container 201 to the heat exchanger unit. Preferably, following an operation of the heat exchanger unit, the mechanism for connecting the container 201 to the heat exchanger unit is configured to lock the container 201 to the heat exchanger unit until the fluid has been evacuated from the inner chamber 202.

Preferably, after a container 201 has been inserted into the heat exchanger unit, fluid is supplied to the inner chamber 202 without pressurising the bag. The pressure around the bag is only increased when the working fluid has cooled to the desired temperature. The pressure is increased to a level that ensures the desired flow rate of the working fluid through the catheter system. Advantageously, since the contents of the inner chamber 202 and the bag are at the same pressure at all times, there is no pressure difference related stress on the walls of the bag.

Preferably, one or more temperature sensors are provided within the bag. This provides an operator with an accurate temperature of the working fluid.

In the system shown in FIG. 1, one or more temperature, pressure and/or flow rate sensors are preferably provided on, or in, the catheter balloon so that these parameters are accurately known. The measured parameters at the balloon are fed back to the heat exchanger unit so that the heat exchanger unit can be automatically controlled to provide a working fluid at a desired flow rate and temperature.

The temperature of the outer surface of the balloon is preferably maintained between +15° C. (288K) and −35° C. (238K) and more preferably between 0 to −30° C. (273K to 243K). Depending on the type of balloon and the heat load, there may be a temperature difference of about 10° C. to 40° C. between the temperatures of the inner and outer surfaces of the balloon and this can be compensated for when controlling the system. In order to provide appropriate temperatures for cryotherapy, the working fluid and pressurising fluid supplied to the inner chamber are preferably liquids over a temperature range of −30° C. to 0° C. and, more preferably, over a temperature range of −70° C. to 50° C.

In the system shown in FIG. 1, the flow of the working fluid is not in a closed loop. In a closed loop system, the flow of the working fluid is recirculated. Such systems either experience the problem of the recirculated fluid becoming contaminated due to its repeated use or the system requires an inline filter to sterilise the working fluid, which results significant increases of the pressure needed to achieve the require pressure and temperature at the balloon. The system shown in FIG. 1 does not experience any of these problems as the working fluid does not flow in a closed loop. The working fluid flows from the catheter system to a waste tank and the working fluid is not recirculated.

As shown on FIG. 1, the system can further comprise a vacuum pump placed between the return working fluid path of the catheter and the waste tank. Such a pump can help increase the flow rate of the working fluid in the catheter and enhance the amount of cryoenergy delivered at the balloon.

The system according to embodiments may comprise one or more computing devices and sensors, in particular temperature, pressure and flow rate sensors, further to those shown in FIG. 1. For example, embodiments may include a computer, such that the system may be software controlled, the computer having one or more controls and/or a user interface such as a graphical user interface. The graphic user interface may inform an operator when the working fluid is ready to be supplied from the console.

In particular if the working fluid is used to inflate and pressurise the catheter balloon, the pressure of the working fluid at the balloon is preferably measured so that it can be accurately controlled. The pressure of the working fluid is dependent on the pressure of the fluid in the inner chamber 202 and the pressure of the working fluid is therefore controllable by controlling the pressure of the fluid in the inner chamber 202.

Sensor signals are preferably used to automatically control the flow rate and/or pressure of the working fluid such that the values of these parameters and the outer surface temperature are within the desired ranges. One or more pressure sensors may also be used to detect any leaks within the catheter by sensing abnormal pressures. One or more temperature sensors may also be used to detect vessel occlusion by the balloon. The operation of the heat exchanger unit, may therefore be automatically controlled by temperature and/or pressure measurements measured at the balloon and/or other parts of the system.

In order to support the sensors, and any other devices, the system may further comprise wires and connectors to one or more power supplies, data interfaces, or other signal processing units, configured to provide a power supply, control signals and to convert sensor signals into data.

The above-described embodiments provide an improved system for providing sterile working fluid to a catheter during cryotherapy. The pressuring of the fluid in the inner chamber 202 allows a uniform driving force to be applied for displacing the contents of a reservoir of sterile working fluid at a controllable flow rate. The flow rate of the working fluid may be adjusted in order to adjust the temperature and pressure within a catheter balloon.

Further embodiments include a number of modifications and variations that can be made to the embodiments as described above.

The system shown in FIG. 1 is an exemplary embodiment for supplying a working fluid to a catheter to cool a target part of a vessel during cryotherapy. It will be understood that some of the specifically described components may not be essential to the operation of the system but are described for context only. Suitable, functionally similar, or equivalent components may be used interchangeably.

In the above-described embodiments, operational temperatures and pressures are provided. However, embodiments are in no way limited to these operational temperatures and pressures. Moreover, the operational temperatures and pressures may be varied depending on the application. In particular, embodiments include the system being operated according to the disclosure in WO2012/140439 A1, the entire contents of which are incorporated herein by reference.

According to a further embodiment, the heat exchanger unit does not have the above-described outer chamber 203. Instead, the fluid supplied for pressurising the inserted container 201 is also the coolant. The heat exchanger unit, and operation of the heat exchanger unit, would be otherwise the same as that for the heat exchanger unit that is shown in FIG. 2 and described throughout the present document. The supply of a coolant fluid that also pressurises the container 201 could be realised by, for example, the fluid that is output from a displacement pump flowing through a heat exchanger to cool the fluid before it is supplied to the inner chamber 202. Although, the heat exchanger may alternatively be arranged to cool the fluid before the fluid flows through the pump, it is preferable for the fluid to be cooled after it has been pressurised as it is generally easier to pump a fluid when it is warm rather than cold due to viscosity effects.

In another embodiment, there is no outer chamber 203 and the fluid in the inner chamber 202 is instead cooled directly by, for example, a thermo-electric element, such as a Peltier cooler, provided on the outer walls of the inner chamber 202. Alternatively, the inner chamber 202 may be cooled by, for example, dry ice.

According to another embodiment, the container 201 does not have a bag for providing a reservoir of the working fluid but instead the container 201 is a rigid cartridge with syringe-like structure. The pressuring of the fluid in the inner chamber 202 actuates the syringe to thereby force the working fluid to flow from the cartridge. Advantageously, such a syringe could be made from metal and therefore have a high thermal conductivity. The working fluid is therefore cooled faster.

According to another embodiment, the container 201 is provided as a rigid syringe with a piston that can be directly driven by an operator of the system. Advantageously, this implementation does not require the above-described pump for pressurising a bag of the container 201.

According to another embodiment, the container 201, and preferably also the umbilical 205, are not at ambient temperature and the container 201 has already been chilled, for example by being stored in a refrigerator.

According to another embodiment, the container 201 is re-filled with sterile working fluid rather than being entirely replaced by a new container 201.

According to another embodiment, the heat exchanger unit comprises a plurality of housings, each housing for providing a sterile working fluid according to any of the above-described embodiments. Advantageously, the heat exchanger unit can be used to perform a plurality of treatments without a container 201 needing to be replaced or the catheter needing replacement in the case of a longer procedure on a single patient. The heat exchanger unit could also be used to supply a greater quantity of working fluid to a catheter system in a single operation than possible if one container 201 only is used.

In the above-described embodiments, the fluid supplied to the inner chamber 202 may be the same type of fluid as used for the working fluid in the container 201.

According to an embodiment, the control of the pressure of the fluid supplied to the inner chamber 202 may be controlled in dependence on a desired heat flux across the catheter balloon. The control is based on the heat flux being dependent on the flow rate of the working fluid and the flow rate of the working fluid being dependent on the pressure of the fluid in the inner chamber 202.

Other embodiments of the invention will be apparent to those skilled in the art from consideration of the specification and practice of the embodiments disclosed herein. It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claims set forth herebelow not be construed as being order-specific unless such order specificity is expressly stated in the claim.

The invention claimed is:

1. An apparatus for supplying a sterile liquid to a catheter for use in cryotherapy, the apparatus comprising:
 a container for containing a sterile liquid;
 a first chamber adapted to receive the container, the container being removable from the first chamber when the container contains the sterile liquid, the first chamber further comprising a fluid port for receiving a surrounding fluid for applying, in use, pressure to the received container; and a second chamber comprising a cooler;

wherein the first chamber is arranged to be in thermal conductivity with the second chamber such that, in use, the contents of the first chamber are cooled by the cooler of the second chamber;

the apparatus further comprising a conduit for providing a supply of the surrounding fluid to the fluid port of the first chamber, wherein the conduit passes through the second chamber and the conduit is arranged in coils in the second chamber.

2. The apparatus according to claim 1, wherein the cooler is provided by a fluid coolant within the second chamber; and the first and second chambers are configured such that there is no fluid communication between the first and second chambers.

3. The apparatus according to claim 2, wherein the fluid coolant is at a temperature of 0° C. or lower.

4. The apparatus according to claim 2, wherein the fluid coolant is ethane.

5. The apparatus according to claim 1, the container comprising a reservoir comprising the sterile liquid, the sterile liquid having a freezing temperature below 0° C.;

wherein, in use, the reservoir is configured to reduce in volume in response to a pressure applied to the container by the surrounding fluid such that the sterile liquid flows out of the container.

6. The apparatus according to claim 5 wherein the reservoir of the container is a compressible bag.

7. The apparatus according to claim 5 further comprising an umbilical conduit for carrying the sterile liquid from the container.

8. The apparatus according to claim 1 further comprising a pressuriser arranged to pressurise the surrounding fluid in the first chamber.

9. The apparatus according to claim 8, wherein the pressuriser is configured to pressurise the surrounding fluid within the first chamber to pressures of at least 20000 kPa.

10. The apparatus according to claim 8, wherein the pressuriser is a positive displacement pump.

11. The apparatus according to claim 8, further comprising a supply of coolant arranged to supply a coolant to the second chamber at a temperature of 0° C. or lower.

12. The apparatus according to claim 1, wherein the container is inserted into the first chamber.

* * * * *